United States Patent [19]

Baum

[11] Patent Number: 4,681,542

[45] Date of Patent: Jul. 21, 1987

[54] RETENTION SYSTEM FOR DENTAL PROSTHESIS

[76] Inventor: Lloyd Baum, 25742 Hinckley St., Loma Linda, Calif. 92354

[21] Appl. No.: 829,921

[22] Filed: Feb. 18, 1986

[51] Int. Cl.⁴ .......................... A61C 13/12; A61C 5/08
[52] U.S. Cl. ..................................... 433/172; 433/219
[58] Field of Search ................... 433/219, 220, 173, 1, 433/172

[56] References Cited

U.S. PATENT DOCUMENTS

| | | | |
|---|---|---|---|
| 2,866,285 | 12/1985 | Gerber | 433/173 |
| 3,514,858 | 6/1970 | Silverman | 433/173 |
| 4,193,194 | 3/1980 | Dalise | 433/173 |
| 4,204,321 | 5/1980 | Scott | 433/173 |

FOREIGN PATENT DOCUMENTS 64601 5/1982 European Pat. Off. .

*Primary Examiner*—Robert Peshock
*Attorney, Agent, or Firm*—Bruce A. Jagger; Natan Epstein

[57] ABSTRACT

An improved telescoping retainer for dental prostheses includes a coping mounted to an abutment tooth and having an endless O-ring groove formed about the outer axial surface of the coping in a plane generally transverse to the coping axis. The coping mates closely with a retainer cavity in the dental prosthesis and has a complementary O-ring groove defined in the retainer surface. A resilient O-ring is fitted over the coping such that the ring cross section is partly received within the coping groove and partly within the retainer groove, thereby forming a resilient interference fit between the dental prosthesis and the coping. A method for making the grooved copings and retainers is disclosed.

4 Claims, 6 Drawing Figures

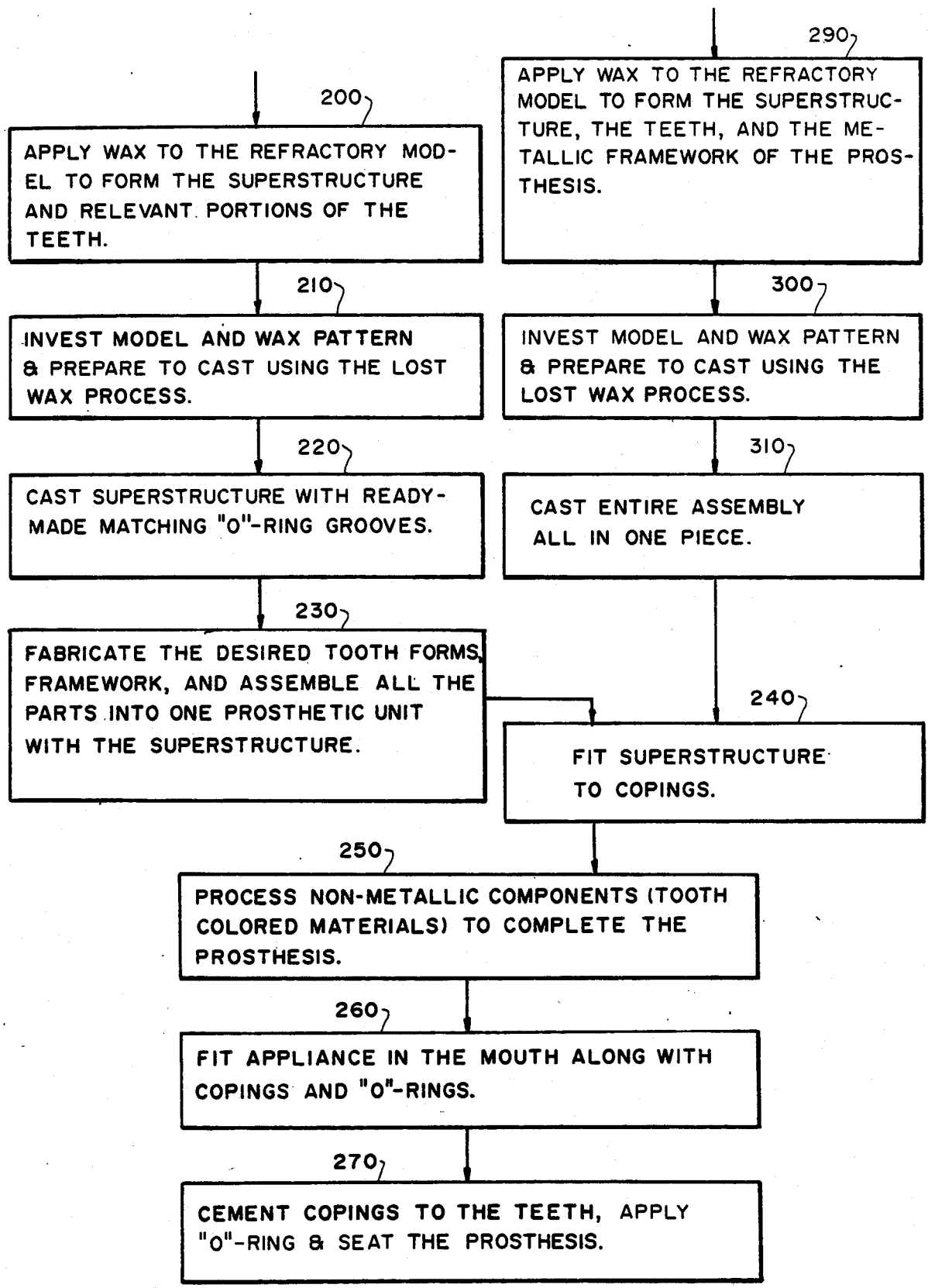

RETENTION SYSTEM FOR DENTAL PROSTHESIS

BACKGROUND OF THE INVENTION

1. Field of the Invention

The present invention is generally directed to devices for removably retaining dentures within the mouth of a user and is more particularly directed to improvements in telescopic mountings for removable dental prostheses.

2. State of the Prior Art

It is known in the prior art to make dental prostheses which are removably attachable so as to facilitate cleaning or repair of the prostheses, and to permit ready access to the underlying abutments and gingivae for hygienic purposes and therapeutic aid.

One known method of detachably securing a dental prosthesis makes use of copings fitted onto underlying abutment teeth. The coping is a primary casting having tapered axial outer surfaces which telescopically fits into a retainer socket formed in the underside of the removable prosthesis. The retainer sockets closely conform in shape to the copings and keep the prosthetic appliance seated on the copings during mastication. A refinement on this retention technique takes advantage of precision machine milling methods for refining the axial surface of the coping to a very smooth and accurately tapered shape. Since the mating retainer sockets in the removable prosthesis are produced from an impression taken directly from the machine milled coping, a very close fit between the coping and retainer surfaces is possible, resulting in a precise prosthesis mounting which is rigid yet removable. Such precision fitting of the telescope retainers, i.e. the socket cavities in the prosthesis to the corresponding copings helps produce a positively retained and stable prosthesis mounting.

It is known that the retentive force between the telescoping retainers in the prosthesis and the corresponding copings is a function of the frictional engagement between the axial coping surfaces and the mating retainer surfaces. The frictional engagement in turn is dependent on the angle of taper of the axial coping surfaces. The greater the angle of taper, the lesser the frictional stress between the telescoping surfaces. Conversely, greater frictional retention can be gained by decreasing the angle of taper. As the taper of the axial coping surface approaches zero, i.e. the coping surfaces become parallel and tubular, the retentive force becomes such that the force of removal of the retainer may exceed the bonding strength of the adhesive used to affix the coping to the underlying abutment tooth, with the result that the coping is pulled off the abutment or the tooth fractures in the attempted removal of the prosthesis. It has been determined and known in the literature that the most favorable angle of taper for the axial coping surfaces is six degrees. Copings with a greater taper become too wide at their lower ends, i.e. at their base adjacent to the gums, creating underlying recesses capable of trapping food particles etc., which then produce a hygiene and esthetic problem. Copings with a lesser rate of taper may be excessively retentive. Thus, a compromise between retentiveness and optimum coping size is found at the aforementioned six degree taper.

Another known approach to the removable mounting of dental prosthesis consists of installing a dental post in the root of two or more spaced apart teeth. Such dental posts are fixed in a hole drilled along the root canal of a tooth which has been severed at the gum line, i.e. only the root of the tooth remaining after the crown has been removed. U.S. Pat. Nos. 4,204,321 and 4,290,755 both to Scott and references cited therein disclose dental posts which have an exposed cylindrical stem in which is formed a circumferential groove into which is fitted an elastomeric O-ring. The denture to be secured has a recess configured for receiving the post and also has a peripheral groove in the post receiving recess shaped and sized to closely fit over the O-ring in an interference fit which retains the denture to the post. The O-ring also serves to partially relieve stresses imposed upon the post by the denture during mastication.

SUMMARY OF THE INVENTION

The present invention advances the state of the art by providing an improved telescope retainer for dental prostheses and a method for making the same. The improved telescope retainer comprises a coping constructed for affixing onto a suitably prepared abutment tooth in the patient's mouth. The coping is a structure which tapers in cross-section along a coping axis. The cross sectional shape of the coping may vary according to the shape of the underlying abutment tooth among other factors. The coping axis extends between a wider base end and an upper end. The coping has an axial outer surface which tapers in cross sectional perimeter along said axis. An endless groove is formed in the outer axial surface of the coping in a plane generally transverse to the coping axis at a location intermediate the base end and the upper end. An O-ring of elastomeric material is axially retained within the groove. The O-ring has a cross-sectional dimension substantially greater than the depth of the groove so that an outer portion of the ring projects radially from the axial coping surface when the ring is fitted in the groove. A dental prosthesis is removably secured to the coping by providing a retainer cavity in the prosthesis having a retainer surface dimensioned for close telescopic mating with the axial coping surface, and second groove provided in the telescoping retainer surface positioned and dimensioned for snuggly receiving the outer portion of the O-ring on the coping. The O-ring thus makes a retentive interference fit between the prosthesis and the coping to supplement the conventional frictional retention between the telescoping surfaces.

The improved mounting requires crown preparation of the underlying abutment tooth in the conventional manner. An impression is taken including the prepared crowns from which a master model is made. The copings are then made and an O-ring groove is formed in one or more of the copings. An impression is then taken of the copings fitted onto the corresponding abutments on the master model with the O-rings in place in the grooved copings so as to make a negative mold using elastomeric impression material. In a variant of this method the dentist may choose to take this impression with the copings on the teeth of the patient rather than on the master model.

A model is then poured in refractory investment material to form the teeth as well as the adjacent oral tissues. A wax pattern is then made over this model to form the superstructure and the teeth. The model and superstructure are then invested and cast to obtain a metallic casting of the superstructure including telescoping retainer sockets with a ready-made groove matching the position and dimension of the O-ring on each coping of the master model. A fitting of the superstructure to the copings may be made outside of the mouth followed by a final fitting inside the patient's mouth after the copings have been cemented to the prepared abutment teeth.

The tapered copings in combination with the resilient O-ring exhibit improved retention characteristics of the prosthesis as compared to tapered copings without such O-ring. The interference fit of the O-ring supplements frictional retention between the telescoping axial surfaces of the retainer socket and coping. As a secondary function, the O-ring may serve to relieve transmission of stress from the prosthesis to the coping and underlying abutment tooth. The retaining system of this invention is hygienic, and the O-ring helps stabilize, center and rigidify the mounting of the prosthesis in relation to the copings. The improved mountings can be made by the average dental technician without difficulty following the method described herein without substantial increase in cost of the procedure. Furthermore, the patient can readily change the O-rings as needed to prolong a snug fit and a securely retentive mounting, thus helping to slow wear of the coping and retainer surfaces.

These and other advantages of the present invention will be better understood by reference to the attached drawings in light of the following detailed description.

DETAILED DESCRIPTION OF THE PREFERRED EMBODIMENT

Figure 1:
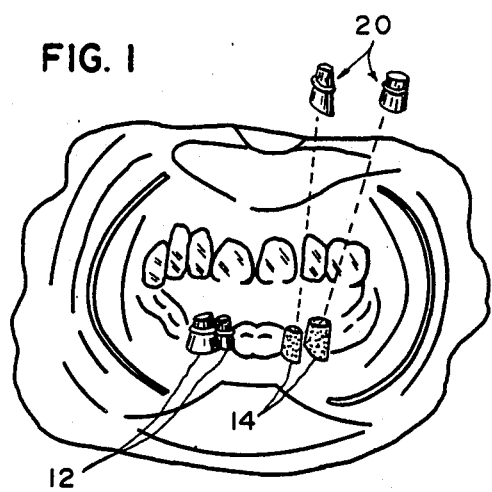
FIG. 1 is a frontal view of a mouth showing lower abutment teeth each being fitted with a coping provided with an O-ring according to the present invention.

With reference to the drawings, FIG. 1 shows by way of example a mouth with four lower teeth prepared as abutments for receiving a denture and securing the same within the mouth. The four abutment teeth include two spaced apart pairs, a first pair including abutments 12 shown with the improved copings of the present invention, while the other pair of abutments 14 as shown as naked crowns shaped and prepared to receive the novel copings 20. Although the drawing shows an O-ring provided for every abutment tooth, optimum function may be obtained with O-rings on less than all abutment teeth.

Figure 2:
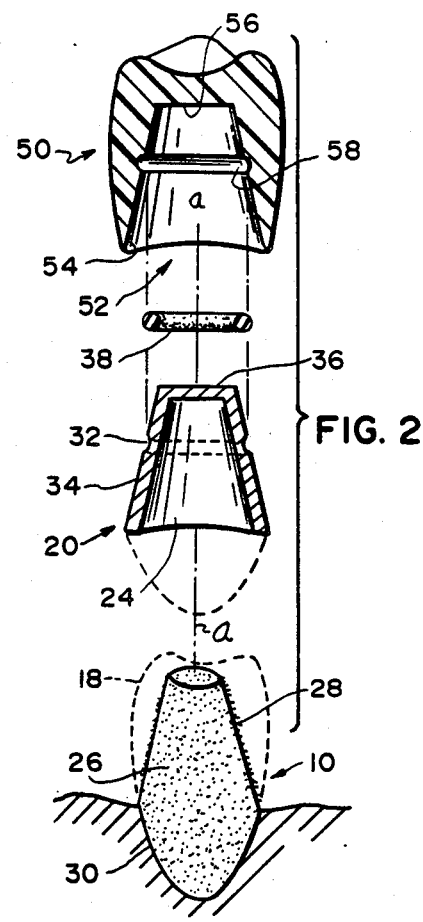
FIG. 2 is an exploded view of an abutment, coping, O-ring and retainer socket.
Figure 3:
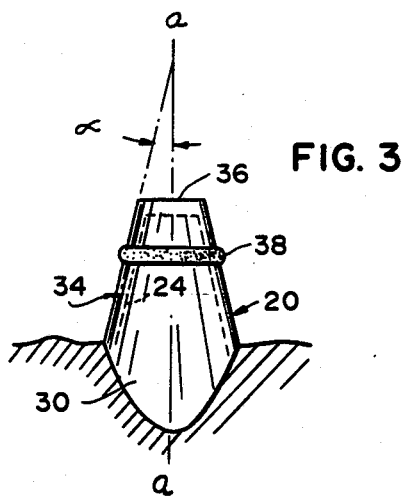
FIG. 3 shows the coping cemented to a corresponding abutment tooth and an O-ring in place on the coping.

Turning to FIG. 2, an abutment tooth 10 has been prepared according to conventional practice by shaping its natural crown 18 shown in dotted lining to the generally tapered, conical shape shown in solid lining. The prepared abutment tooth has a generally conical outer axial surface 26 truncated at its upper end to define a transverse end surface 22. A coping 20 is formed with a coping axis a—a and an internal coping surface 24 which fits over the axial surface 26 of the abutment 10. The coping 20 is cemented by means of layer 28 of a suitable dental adhesive which securely bonds the coping 20 to the abutment 10. The coping 10 is closed at its upper end and the base of the coping follows the gum line 30 of the abutment so as to substantially cover the underlying abutment tooth as best seen in FIG. 3. The outer axial surface 34 of the coping 20 generally follows the shape of the prepared abutment 10 tapering in cross section from its base end at the gumline 30 and terminates in a generally planar transverse upper end surface 36 of reduced cross section. An endless radial groove 32 is formed in the outer axial surface 34 of the coping 20 in a plane which is transverse to the coping axis shown as a dotted vertical line a-a in FIGS. 2 and 3. An O-ring 38 having a preferably circular cross-section and made of a suitable, substantially inert elastomeric material is stretched over the coping 20 and set into the O-ring groove 32 as shown in FIG. 3. The O-ring 38 is selected to have a normal unexpanded inner diameter smaller than the perimeter defined by the groove 32, such that the ring 38 is stretched about the coping and retained within the groove 32 by its tendency to resiliently return to its normal, unstretched state.

Figure 5:
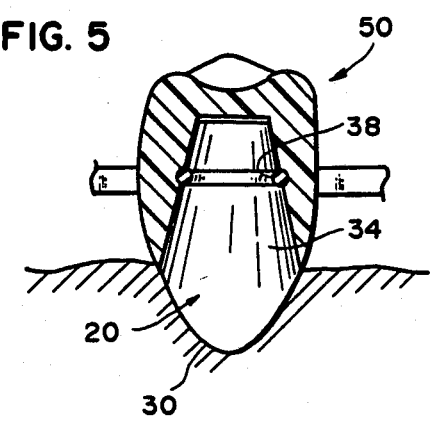
FIG. 5 shows the complete novel mounting comprising a prosthetic tooth in which is formed a retainer socket telescopically fitted onto a coping provided with an O-ring.

The axial coping wall 34 is tapered from a larger base cross-section at the gum line 30 to a reduced cross-sectional dimension at the upper end surface 36. The angle of taper of the axial coping wall, angle alpha in FIG. 3, is selected (e.g., a 6 degree angle) to provide optimum retaining characteristics for a prosthetic tooth 50 seen in FIG. 2 in exploded relationship to the coping 20 and abutment 10. A retainer cavity or socket 52 is defined in the prosthetic tooth 50 including an internal axial socket surface 54 closely conforming to the outer axial coping surface 34, and having a end wall 56 which lies against the end surface 36 of the coping when the prosthesis 50 is telescopically seated onto the coping 20. The axial retainer surface 54 tapers at an angle alpha substantially identical to the taper of coping 20 so as to make a close, preferably precision fit with the coping surface 34. A complementary O-ring groove 58 is formed in the axial retainer surface 52, i.e. in the internal surface of the socket 52, opposite to and in axial alignment with the O-ring groove 32 in the coping 20. Thus, the retainer groove 58 is in alignment with the coping groove 32 when the prosthesis 50 is telescoped onto the coping 20, as shown in FIG. 5, and the O-ring 38 lies partly in the coping groove and partly in the retainer groove.

As has been explained, the retentive force between the prosthesis 50 and coping 20 is in substantial part determined by the taper angle alpha. As the angle alpha increases, the retentive frictional force between the retainer surface 52 and axial coping surface 34 decrease. An optimal angle is found at which adequate retaining force is exerted but not such as to break the adhesive bond 28 between the coping and abutment 10 upon attempted removal of the prosthesis. Thus, a practical limit to the usable retaining force of the mounting is set by the strength of the adhesive bond 28 and ultimately by the strength of the underlying abutment tooth. Improved retention is obtained according to the present invention by providing the resilient O-ring 38 in the manner illustrated and described. When the prosthetic tooth 50 is telescoped onto the coping 20, the O-ring 38 is seated on its radially inner side within the coping groove 32 while its radially outer portion projects radially outwardly from the groove 32 and into the complementary retainer groove 58. The O-ring 38 interlocks the prosthesis 50 and coping 20 against axial telescopic disengagement and thereby enhances retention of the prosthesis 50 as compared to a mounting which relies on nothing more than the frictional force between the retainer surface 54 and coping surface 34.

Figure 4:
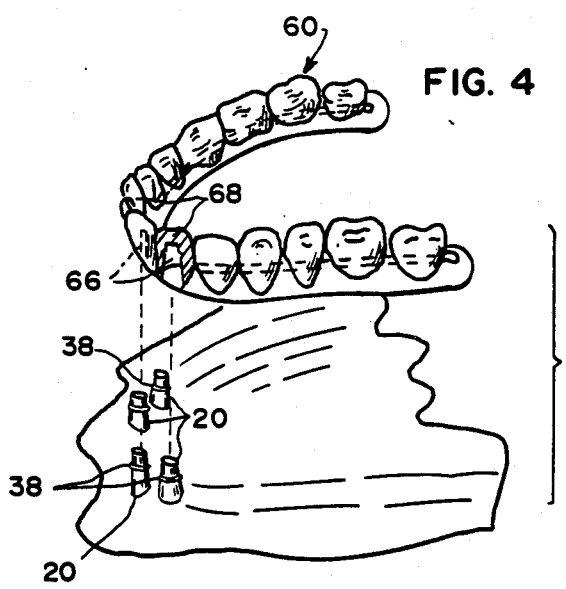
FIG. 4 shows a dental prosthesis being fitted onto four copings each provided with an O-ring according to this invention.

In a practical denture or prosthesis, more than one abutment, and corresponding coping and retainer, are required. In the example of FIG. 4 a denture 60 is retained by means of four abutments, each having a tapered coping 20 and a corresponding O-ring 38. For each abutment, a corresponding retainer socket or cavity 66, (of which only two are shown in FIG. 4 in dotted lining) is formed in a retainer tooth 68 in the denture 60. Each retainer cavity 66 is formed with a complementary groove such as 58 in FIG. 2 dimensioned and positioned to receive the radially outer portion of the O-ring 20 on the corresponding abutment tooth.

It will be appreciated that the O-rings 64 can be readily removed from the coping by the patient upon removal of the denture 60, to allow cleaning or replacement of the O-rings 20 as needed, thereby maintaining the interlock between the copings and prosthesis against degradation of the elastomeric O-rings.

Figure 6:
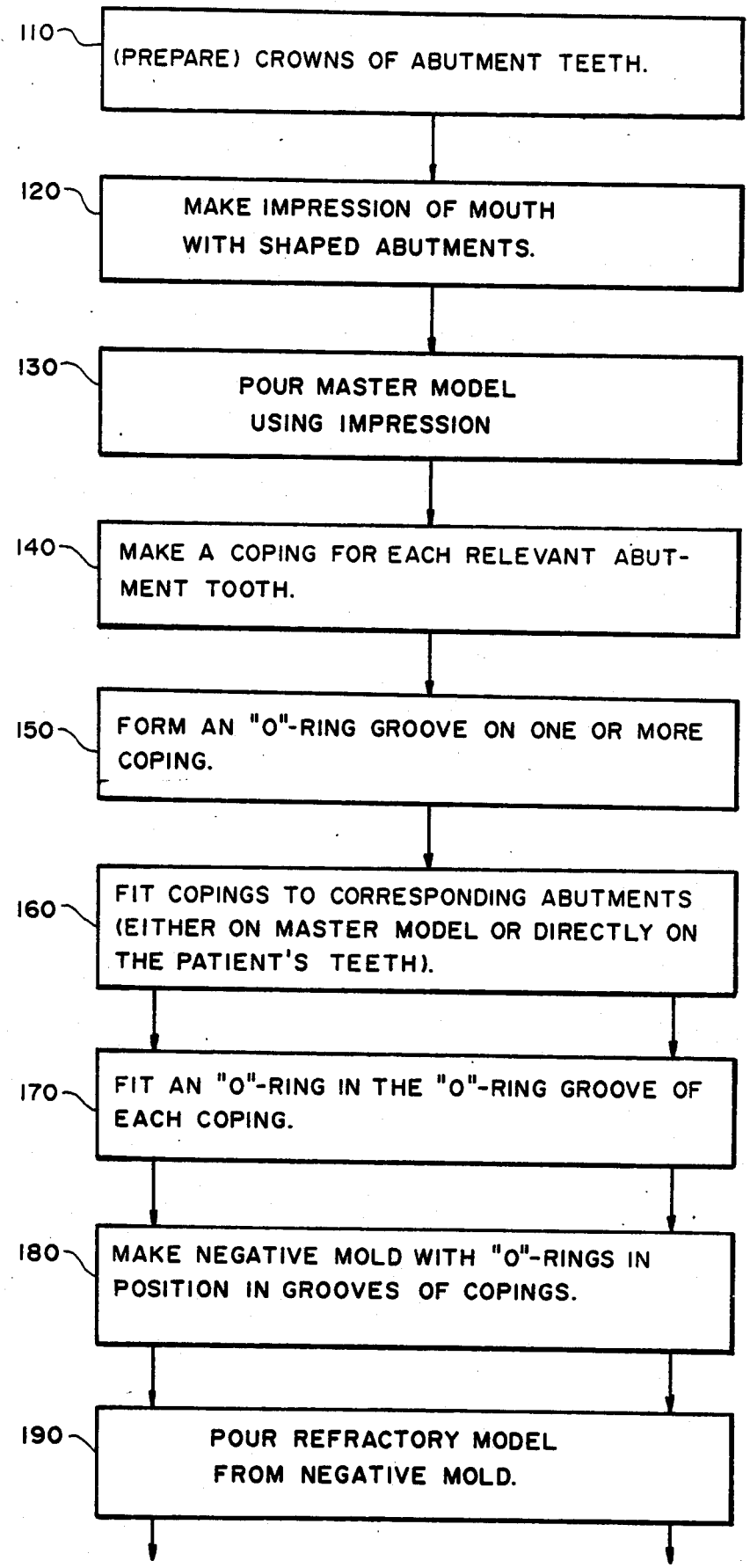
FIG. 6 is a flow chart illustrating the process for making the improved prosthesis.

The process for making the improved prosthesis retainer is illustrated in the flow chart of FIG. 6. Step 110 consists of crown preparation of the abutment teeth in the patient's mouth followed by step 120 where a coping for each prepared abutment tooth is made in accordance with conventional methods, as by taking an impression of the prepared crowns to make a master model in step 130 and then making copings based on the master model in step 130 and then making copings based on the master model as step 140. The novel process departs from the prior art in that an O-ring groove is formed as step 150 on the outer axial surface of either all or selected copings. The copings are then fitted either onto the master model or directly on the patient's abutment teeth as step 160, and an appropriately sized elastomeric O-ring is fitted into the groove of each grooved coping as step 170. Step 180 involves taking an impression using elastomeric impression material to obtain a negative mold of the master model with both the copings and the O-rings in place. The negative mold thus obtained will have retainer cavities or sockets 52 with the complementary O-ring grooves 58 positioned and dimensioned for receiving the outer periphery of the O-rings 38 on the copings 20.

In step 190 a model is poured from the negative mold in a refractory investment material. The refractory model is then waxed to form the superstructure and relevant portions of the teeth as step 200, followed by investing of both the model and wax pattern in step 210 in preparation for casting using the lost wax process. In the following step 220 the superstructure is cast with the ready made complementary O-ring grooves in the retainer cavities or sockets ready to receive the outer periphery of the O-rings on the copings. In step 230 the desired tooth forms and framework are fabricated and assembled with the superstructure into one prosthetic unit, and the superstructure is fitted to the copings as step 240. The prosthetic appliance is then completed by processing of non-metallic components such as tooth colored materials in step 250. At this stage the prosthesis is ready for fit testing in the patient's mouth along with the copings and O-rings in step 260. If the fit is satisfactory, the copings may be cemented to their corresponding abutment teeth in the patient's mouth, the O-rings mounted onto their corresponding copings, and the prosthesis seated onto the copings in step 270.

As a variant of the aforedescribed procedure, the copings prepared in step 140 are fitted directly onto the patient's abutment teeth in step 280 instead of onto the master model in step 160. Steps 170, 180 and 190 are then taken as described, but instead of step 200, the process continues with alternate step 290 where wax is applied to the refractory model to form the superstructure, the teeth and the metallic framework of the prosthesis. In the following step 300, the waxed refractory model is invested and prepared for casting using the lost wax process, and the entire assembly is cast all in one piece in step 310 as opposed to separate fabrication of the tooth forms and framework and assembly of the separate components with the superstructure in step 230 of the earlier described process. The alternate method concludes with steps 240 through 270 as described above.

The foregoing process in either variant can be readily practiced by a dental technician possessed of average skills without substantially adding to the cost or time required to make a prosthesis, yet obtaining substantial improvement in the retention and wear characteristics of the completed prosthetic structure. The improved retaining mounting is hygienic in that it can be readily cleaned at frequent intervals because of the easy removal of the O-rings, and can also be easily maintained by the patient through regular replacement of the O-rings as their condition may require.

In addition to the improved retentive capability of the novel telescope mount, further improvement is made over prior telescopic retainers in that the O-rings resiliently interposed between the coping and the prosthetic retainer element may also serve to partially absorb shock and stress transmitted onto the coping. Still further, the resilient O-rings serve to center the retainer cavity over the coping if any looseness develops therebetween, thereby stabilizing and rigidifying the prosthesis against loose play in relation to the copings. In prior art telescopic mountings for dental prostheses the retainer should ideally make a perfect fit with the axial coping surface, but this goal is not always achieved and even if initially obtained such perfect fit deteriorates through wear of the coping and retainer surfaces. Provision of the elastomeric O-ring as disclosed herein improves the original fit and compensates for inaccuracy in the fit of the telescoping surfaces developed during wear of the prosthetic appliance, assuring improved retentive characteristics of the telescope mounting as compared to prior art telescope mountings which such O-ring even after the original fit deteriorates due to wear of the telescope surfaces.

While particular embodiments of the invention have been shown and illustrated for purposes of clarity and by way of example only, it will be understood that many changes, substitutions and modifications can be made by those possessed of ordinary skill in the art without departing from the spirit and scope of the invention which is defined only by the following claims.

What is claimed is:

1. An improved telescope retainer for dental prostheses comprising:
    a coping affixed at a lower end to an abutment tooth, said coping having a coping axis and an upwardly tapering outer axial surface;

a groove in said axial surface encompassing said coping in a plane generally transverse to said coping axis;

an O-ring of elastomeric material stretched about said coping and elastically retained in said groove, said O-ring having a cross-sectional diameter substantially greater than the depth of said groove such that an outer portion of said ring projects from said axial coping surface; and a prosthesis having a retainer cavity including a retainer surface closely telescopically mateable onto said axial coping surface, there being a complementary groove in said retainer surface shaped to closely match and receive said outer portion of the O-ring, said O-ring thus making a resilient retentive interference fit between said prosthesis and said coping.

2. A process for making an improved retention system for dental prostheses comprising the steps of:

preparing the crowns of one or more abutment teeth;

taking an impression of the prepared crowns to make a master model;

making a coping for each abutment on the master model;

forming an O-ring groove in the outer axial surface of one or more of said copings transversely to the vertical axis of the coping;

fitting the copings to the corresponding abutments on the master model;

stretching an appropriately sized elastomeric O-ring about each said grooved coping such that the O-ring is resiliently retained in said groove, each said O-ring having a cross-sectional diameter greater than the depth of said O-ring groove;

taking an impression to obtain a negative mold of the master model with the copings and the O-rings in place, the negative mold thus obtained having retainer cavities with O-ring grooves closely matching the protruding outer portion of the O-rings and positioned and dimensioned for receiving the protruding outer periphery of the O-ring on each of said copings;

pouring a model from the negative mold in a refractory investment material;

casting the superstructure with the ready made matching O-ring groove in the retainer cavities; and fabricating the desired tooth forms and assembling the same with the superstructure into one prosthetic unit.

3. A process for making an improved retention system for dental prostheses comprising the steps of:

preparing the crowns of the abutment teeth;

making a coping for each of said abutment teeth;

forming an O-ring groove in one or more of said copings, each O-ring groove fully encompassing each of said one or more copings;

fitting said copings to the abutment teeth in the patient's mouth;

elastically fitting an O-ring of resilient elastomeric material in each O-ring groove said O-ring having a cross-sectional diameter greater than the depth of said O-ring groove;

making a negative mold of the copings in place in the patient's mouth with the O-rings in place, the negative mold thus obtained having retainer cavities with O-ring grooves closely matching the protruding outer portions of the O-rings and positioned and dimensioned for receiving the outer periphery of the O-ring on said copings;

pouring a refractory model from the negative mold;

waxing the refractory model to form the superstructure, teeth and metallic framework of the prosthesis; and investing and casting the entire assembly of refractory model and wax pattern as one unit.

4. The method of claim 3 further comprising the steps of fitting the superstructure to the copings;

completing the prosthesis as required by processing of non-metallic components; and cementing the copings to the patient's abutment teeth, elastically fitting O-rings of elastomeric material to copings grooved therefor, and seating the prosthesis of the copings and O-rings whereby said O-rings form a resilient retentive interference fit between said prosthesis and said copings.

* * * * *